(12) United States Patent
Shintou et al.

(10) Patent No.: US 7,985,288 B2
(45) Date of Patent: Jul. 26, 2011

(54) COLORANT COMPOUND AND INK INCLUDING THE COLORANT COMPOUND

(75) Inventors: Taichi Shintou, Saitama (JP); Yasuaki Murai, Kawasaki (JP); Masashi Hirose, Machida (JP); Takeshi Miyazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 113 days.

(21) Appl. No.: 12/577,552

(22) Filed: Oct. 12, 2009

(65) Prior Publication Data

US 2010/0089285 A1    Apr. 15, 2010

(30) Foreign Application Priority Data

Oct. 14, 2008   (JP) ................................. 2008-265177

(51) Int. Cl.
*C09D 11/02*   (2006.01)
*C09B 29/36*   (2006.01)
(52) U.S. Cl. .................... 106/31.48; 534/752
(58) Field of Classification Search ............... 106/31.48; 534/752
See application file for complete search history.

(56) References Cited

U.S. PATENT DOCUMENTS

| | | | | |
|---|---|---|---|---|
| 2,432,419 A | * | 12/1947 | Heimbach | 534/705 |
| 3,420,813 A | * | 1/1969 | Senn et al. | 534/752 |
| 3,847,919 A | * | 11/1974 | Knowles et al. | 534/752 |

(Continued)

FOREIGN PATENT DOCUMENTS

JP    S38-013641 B    7/1963

(Continued)

OTHER PUBLICATIONS

Lectures on New Experimental Chemistry 14—Synthesis and Reaction of Organic Compounds V, p. 2605 (by Japan Chemical Society, published by Maruzen).

(Continued)

*Primary Examiner* — Helene Klemanski
(74) *Attorney, Agent, or Firm* — Canon U.S.A., Inc., IP Division

(57) ABSTRACT

The invention provides a colorant compound represented by the general formula (I) below.

General Formula (I)

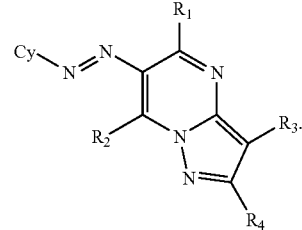

In the general formula (I), $R_1$ and $R_2$ represent independently from each other a species selected from at least one of an alkyl group, an aryl group, an aralkyl group, an alkoxy group, an aryloxy group, an amino group, and a hydroxyl group. $R_3$ and $R_4$ represent independently from each other a species selected from at least one of a hydrogen atom, an alkyl group, an aryl group, a heterocycle group, an amino group, a hydroxyl group, a cyano group, an alkoxy group, an alkylsulfanyl group, a carboxylic acid group, a carboxylic acid ester group, a carboxylic acid thioester group, a carbamoyl group, a nitro group, and a halogen atom. $R_3$ and $R_4$ may optionally be bonded together to form an aromatic ring. Cy represents an aryl group having at least one anionic group.

11 Claims, 1 Drawing Sheet

U.S. PATENT DOCUMENTS

| | | |
|---|---|---|
| 3,907,799 A | 9/1975 | O'Brien |
| 3,980,632 A * | 9/1976 | Henzi .................... 534/610 |
| 4,367,173 A * | 1/1983 | Kanter .................... 534/752 |
| 5,608,041 A * | 3/1997 | Schefczik et al. ........... 534/752 |
| 5,612,465 A * | 3/1997 | Schefczik et al. ........... 534/752 |
| 6,582,502 B2 * | 6/2003 | Fujiwara ................ 106/31.48 |
| 6,723,835 B1 | 4/2004 | Millard et al. |
| 6,855,195 B2 * | 2/2005 | Nishita et al. ............ 106/31.48 |
| 7,608,140 B2 * | 10/2009 | Link et al. .............. 106/31.48 |
| 2009/0293764 A1 * | 12/2009 | Hasegawa et al. ........ 106/31.48 |
| 2009/0293765 A1 * | 12/2009 | Hasegawa et al. ........ 106/31.48 |

FOREIGN PATENT DOCUMENTS

| | | |
|---|---|---|
| JP | 5-17470 A | 1/1993 |
| JP | 6-287459 A | 10/1994 |
| JP | 11-078258 A | 3/1999 |
| JP | 2003-510398 T | 3/2003 |

OTHER PUBLICATIONS

Chem. Rev., 91, 165 (1991).

J. Heterocycl. Chem., vol. 12, p. 1199-1205 (1975).

* cited by examiner

COLORANT COMPOUND AND INK INCLUDING THE COLORANT COMPOUND

BACKGROUND OF THE INVENTION

1. Field of the Invention

The present invention relates to a colorant compound and an ink including the colorant compound.

2. Description of the Related Art

Water-soluble dyes are generally used as colorants in ink jet recording liquids (inks), but a problem associated with recorded images formed by inks including water-soluble dyes is that the images have poor storage stability. Thus, problems are associated with discoloration of images caused by solar light or various types of illumination light (light fastness) or discoloration of images caused by oxidizing gases (ozone, $NO_x$, $SO_x$) contained in very small amounts in the atmosphere (gas resistance).

A pyridone azo colorant compound has been suggested as a water-soluble dye for ink jet recording with the object of resolving the above-described problems (JP-W No. 2003-510398).

A colorant compound having an azo group in a 3 position of a pyrazolopyrimidine site has also been suggested as a colorant compound having a hue similar to that of the pyridone azo colorant compound (JP-A No. 06-287459).

A method for manufacturing a 6-phenyl azopyrazolo derivative as a pyrazolopyrimidine colorant compound having an azo group in a 6 position (see JP-B No. 38-13641) and xanthine oxidase inhibitor (U.S. Pat. No. 3,907,799) have also been disclosed, but not with the object of resolving the above-described problems.

A pyrazolopyrimidine colorant compound that is used as a thermosensitive transfer recording material has also been disclosed (JP-A No. 11-78258).

SUMMARY OF THE INVENTION

Aspects of the invention provide a colorant compound represented by the general formula (I) below.

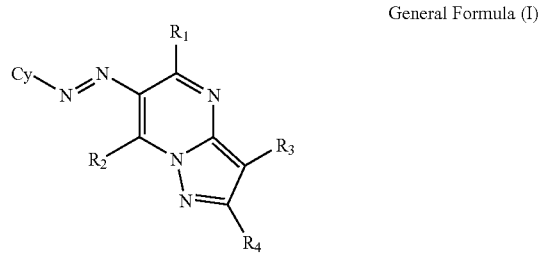

General Formula (I)

In the general formula (I), $R_1$ and $R_2$ represent independently from each other a species selected from at least one of an alkyl group, an aryl group, an aralkyl group, an alkoxy group, an aryloxy group, an amino group, and a hydroxyl group. $R_3$ and $R_4$ represent independently from each other a species selected from at least one of a hydrogen atom, an alkyl group, an aryl group, a heterocycle group, an amino group, a hydroxyl group, a cyano group, an alkoxy group, an alkylsulfanyl group, a carboxylic acid group, a carboxylic acid ester group, a carboxylic acid thioester group, a carbamoyl group, a nitro group, and a halogen atom. $R_3$ and $R_4$ may optionally be bonded together to form an aromatic ring. Cy represents an aryl group having at least one anionic group.

Another aspect of invention also provides an aqueous ink, in particular an ink jet ink, including the colorant compound represented by the general formula (I).

In accordance with aspects of the invention, a colorant compound with good light fastness and gas resistance is provided. Furthermore, in accordance with the invention, by using the colorant compound having the structure represented by the general formula (I) as a colorant for ink, it is possible to provide an ink, in particular an ink for ink jet recording, that has high storage stability, and can form images that excel in light fastness and gas resistance.

DESCRIPTION OF THE EMBODIMENTS

Figure 1:
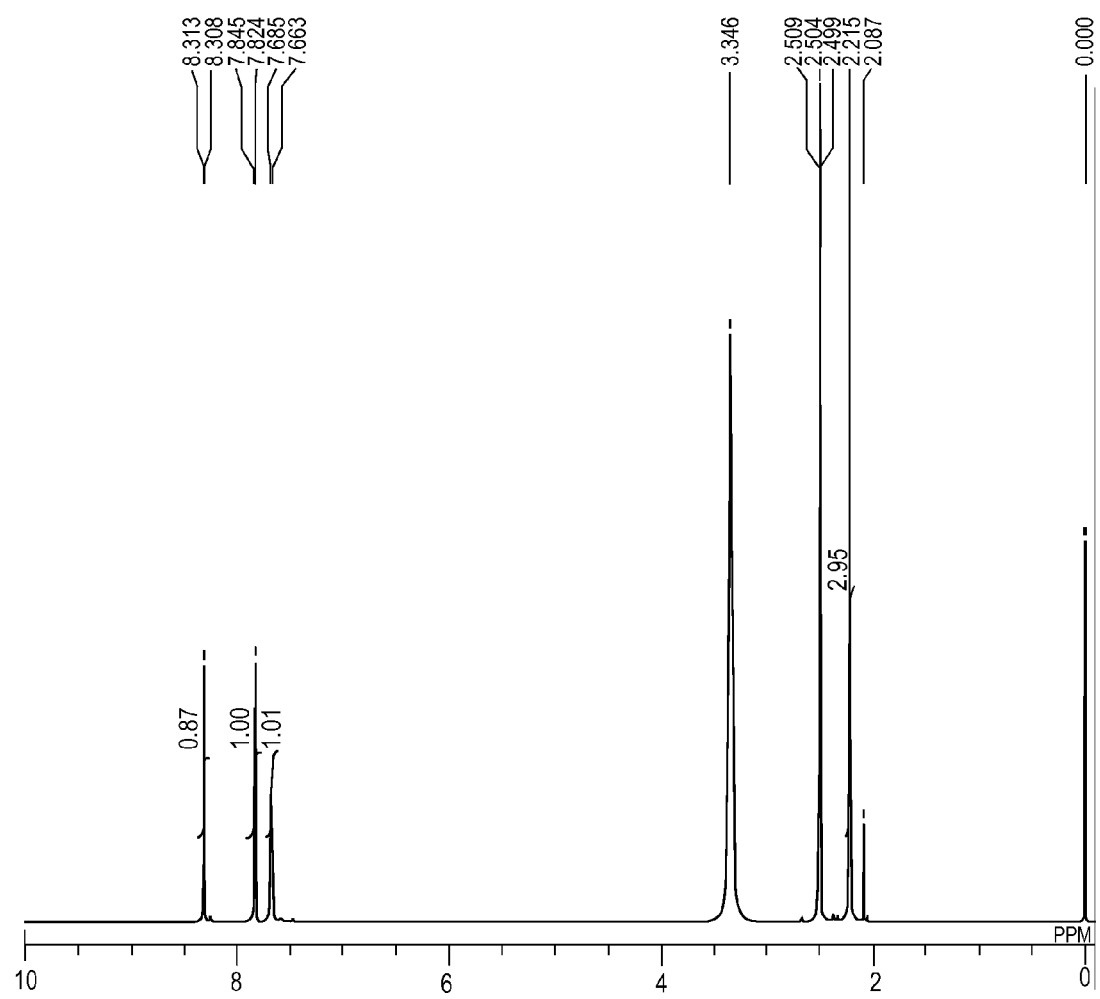
FIG. 1 shows a $^1$H NMR spectrum (400 MHz, DMSO-$d_6$, room temperature) of the colorant compound (I-1) in accordance with aspects of the invention.

The examination conducted by the inventors demonstrated that the colorant compound disclosed in JP-W No. 2003-510398 has insufficient weather resistance, in particular light fastness. The colorant compound disclosed in JP-A No. 06-287459 has an azo substituent in a 3 position of a pyrazolopyrimidine site, but weather resistance, in particular light fastness and gas resistance are insufficient. The colorant compounds disclosed in JP-B No. 38-13641 and U.S. Pat. No. 3,907,799 are both used as drugs and, therefore, not suitable as inks for ink jet recording in terms of weather resistance and solubility in water. The colorant compound disclosed in JP-A No. 11-78258 includes two azo groups obtained by substituting azo groups in 3 and 6 positions of a pyrazolopyrimidine skeleton, and this colorant compound is not suitable for use as an ink for ink jet recording.

Aspects of the invention resolve the above-described problems inherent to the related art and provide a colorant compound with high light fastness and gas resistance. Aspects of the invention also provide an ink that forms images with excellent storage stability when used as ink for ink jet recording.

Aspects of the invention will be described below in greater detail on the basis of exemplary embodiments thereof.

The inventors have conducted a comprehensive research aimed at the resolution of the above-described problems of the related art. The results obtained demonstrated that a colorant compound represented by the following general formula (I) forms images with good light fastness and gas resistance, and when the colorant compound represented by the general formula (I) below is used as a coloring material for ink, an ink with high storage stability can be obtained.

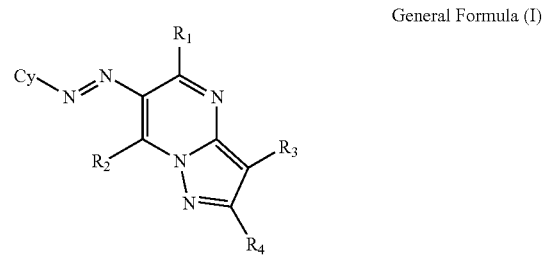

General Formula (I)

In the general formula (I), $R_1$ and $R_2$ represent independently from each other a species selected from at least one of an alkyl group, an aryl group, an aralkyl group, an alkoxy group, an aryloxy group, an amino group, and a hydroxyl group. $R_3$ and $R_4$ represent independently from each other a species selected from at least one of a hydrogen atom, an alkyl group, an aryl group, a heterocycle group, an amino group, a hydroxyl group, a cyano group, an alkoxy group, an alkylsulfanyl group, a carboxylic acid group, a carboxylic acid ester group, a carboxylic acid thioester group, a carbamoyl group, a nitro group, and a halogen atom. $R_3$ and $R_4$ may optionally be bonded together to form an aromatic ring. Cy represents an aryl group having at least one anionic group.

The alkyl group in $R_1$ and $R_2$ in the general formula (I) is not particularly limited, and examples thereof include linear, branched, or cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group in $R_1$ and $R_2$ is not particularly limited, and examples thereof include a monocyclic or polycyclic aryl group having 6 to 14 members, such as a phenyl group, a naphthyl group, a phenanthryl group, and an anthracenyl group.

The aralkyl group in $R_1$ and $R_2$ is not particularly limited, and examples thereof include a benzyl group and a phenethyl group.

The alkoxy group in $R_1$ and $R_2$ is not particularly limited, and examples thereof include an alkoxy group having 1 to 20 carbon atoms such as a methoxy group, an ethoxy group, a propoxy group, a butoxy group, a pentyloxy group, a decyloxy group, a hexyloxy group, a heptyloxy group, an octyloxy group, a nonyloxy group, a decyloxy group, a dodecyloxy group, and an octadecyloxy group.

The aryloxy group in $R_1$ and $R_2$ is not particularly limited, and examples thereof include a phenoxy group and a naphthoxy group.

The amino group in $R_1$ and $R_2$ is not particularly limited, and examples thereof include a unsubstituted amino group; a monosubstituted amino group such as an N-methylamino group, an N-butylamino group, an N-hexylamino group, an N-tetradecylamino group, an N-phenylamino group, and an N-naphthylamino group; a disubstituted amino group such as an N,N-dimethylamino group, an N,N-diethylamino group, an N,N-diphenylamino group, an N,N-methylpropylamino group; a carbonylamino group such as an acetylamino group, an ethylcarbonylamino group, a tert-butylcarbonylamino group, a benzoylamino group, a naphthoylamino group, and a methoxycarbonylamino group; and a sulfonylamino group such as a methylsulfonylamino group, an ethylsulfonylamino group, a tert-butylsulfonylamino group, and a iso-propoxysulfonylamino group.

$R_1$ and $R_2$ may have a substituent which is not particularly limited, provided that water solubility or storage stability of the colorant compound is not substantially degraded. Examples of suitable substituents include an alkyl group such as a methyl group, an ethyl group, an n-propyl group, an isopropyl group, an n-butyl group, an isobutyl group, a sec-butyl group, and a tert-butyl group; an aryl group such as a phenyl group, and a naphthyl group; an alkoxy group such as a methoxy group, an ethoxy group, and a butoxy group; an aryloxy group such as a phenoxy group and a naphthyloxy group; a disubstituted amino group such as a dimethylamino group, an N-ethyl-N-phenylamino group, and a diphenylamino group; an acyl group such as an acetyl group and a benzoyl group; a sulfonyl group; a carbamoyl group; a sulfamoyl group; a heterocyclic group such as a pyridyl group, a triazinyl group, and a benzothiazolyl group; a nitro group; and a halogen atom such as a fluorine atom, a chlorine atom, a bromine atom, and a iodine atom.

$R_1$ and $R_2$ can be independently and randomly selected from the substituents listed above. Examples thereof are presented below. Thus, any substituent selected from an alkyl group having 1 to 4 carbon atoms, an alkoxy group, an amino group, and a hydroxyl group may be provided. In one aspect, either of $R_1$ or $R_2$ be a hydroxyl group, such a selection may provide light fastness and ozone resistance. Both $R_1$ and $R_2$ may also be hydroxyl groups; in this case, excellent light fastness and ozone resistance are obtained.

The alkyl group in $R_3$ and $R_4$ in the general formula (I) is not particularly limited, and examples thereof include linear, branched, or cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group in $R_3$ and $R_4$ is not particularly limited, and examples thereof include a monocyclic or polycyclic aryl group having 6 to 14 members, such as a phenyl group, a naphthyl group, a phenanthryl group, and an anthracenyl group.

The heterocyclic group in $R_3$ and $R_4$ is not particularly limited, and examples thereof include monocyclic or dicyclic heterocyclic groups having 4 to 10 members and containing 1-4 atoms selected from nitrogen, oxygen, and sulfur. Specific examples include a pyridyl group, a pyrazyl group, a pyrimidyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

The amino group in $R_3$ and $R_4$ is not particularly limited, and examples thereof include a unsubstituted amino group; a monosubstituted amino group such as an N-methylamino group, an N-butylamino group, an N-hexylamino group, an N-tetradecylamino group, an N-phenylamino group, and an N-naphthylamino group; a disubstituted amino group such as an N,N-dimethylamino group, an N,N-diethylamino group, an N,N-diphenylamino group, an N,N-methylpropylamino group; a carbonylamino group such as an acetylamino group, an ethylcarbonylamino group, a tert-butylcarbonylamino group, a benzoylamino group, a naphthoylamino group, and a methoxycarbonylamino group; and a sulfonylamino group such as a methylsulfonylamino group, an ethylsulfonylamino group, a tert-butylsulfonylamino group, and a iso-propoxysulfonylamino group.

The alkoxy group in $R_3$ and $R_4$ is not particularly limited, and examples thereof include alkoxy groups having 1 to 20 carbon atoms such as a methoxy group, an ethoxy group, a propoxy group, a butoxy group, a pentyloxy group, a decyloxy group, a hexyloxy group, a heptyloxy group, an octyloxy group, a nonyloxy group, a decyloxy group, a dodecyloxy group, and an octadecyloxy group.

The alkylsulfanyl group in $R_3$ and $R_4$ is not particularly limited, and examples thereof include a thiomethyl group, a thioethyl group, a thiopropyl group, a thiobutyl group, and a thuiophenyl group.

The ester group in $R_3$ and $R_4$ is not particularly limited, and examples thereof include a methyl ester group, an ethyl ester group, a propyl ester group, a tert-butyl ester group, a pentyl ester group, and a phenyl ester group.

The thioester group in $R_3$ and $R_4$ is not particularly limited, and examples thereof include a thioacetyl group, an ethylthiocarbonyl group, a propylthiocarbonyl group, a tert-butylthiocarbonyl group, a pentylthiocarbonyl group, and a thiobenzoyl group.

The carbamoyl group in $R_3$ and $R_4$ is not particularly limited, and examples thereof include an unsubstituted carbamoyl group and a substituted carbamoyl group such as N-methylcarbamoyl group, N-(tert-butyl)carbamoyl group, and N,N-dimethylcarbamoyl group.

The halogen atom in $R_3$ and $R_4$ is not particularly limited, and examples thereof include a fluorine atom, a chlorine atom, a bromine atom, and a iodine atom.

The ring that may be formed by $R_3$ and $R_4$ bonded together is not particularly limited, and examples thereof include an aromatic ring having 3 to 10 carbon atoms such as a benzene ring and a naphthalene ring, a saturated ring such as a cyclopentane ring and a cyclobutane ring, a partially saturated ring such as a cyclopentene ring and a cyclohexane ring, and a hetero ring such as a pyridine ring and a pyrimidine ring. These rings may have a substituent which is not particularly limited, provided that water solubility or storage stability of the colorant compound is not substantially degraded. Examples of suitable substituents include an alkyl group such as a methyl group, an ethyl group, an n-propyl group, an isopropyl group, an n-butyl group, an isobutyl group, a sec-butyl group, and a tert-butyl group; an aryl group such as a phenyl group, and a naphthyl group; an alkoxy group such as a methoxy group, an ethoxy group, and a butoxy group; an aryloxy group such as a phenoxy group and a naphthyloxy group; a disubstituted amino group such as a dimethylamino group, an N-ethyl-N-phenylamino group, and a diphenylamino group; an acyl group such as an acetyl group, and a benzoyl group; a sulfonyl group; a carbamoyl group; a sulfamoyl group; a heterocyclic group such as a pyridyl group, a triazinyl group, and a benzothiazolyl group; a nitro group; a halogen atom such as a fluorine atom, a chlorine atom, a bromine atom, and a iodine atom: a carboxylic acid group; and a sulfonic acid group.

$R_3$ and $R_4$ may have a substituent which is not particularly limited, provided that water solubility or storage stability of the colorant compound is not substantially degraded. Examples of suitable substituents include an alkyl group such as a methyl group, an ethyl group, an n-propyl group, an isopropyl group, an n-butyl group, an isobutyl group, a sec-butyl group, and a tert-butyl group; an aryl group such as a phenyl group, and a naphthyl group; an alkoxy group such as a methoxy group, an ethoxy group, and a butoxy group; an aryloxy group such as a phenoxy group and a naphthyloxy group; a disubstituted amino group such as a dimethylamino group, an N-ethyl-N-phenylamino group, and a diphenylamino group; an acyl group such as an acetyl group, and a benzoyl group; a sulfonyl group; a carbamoyl group; a sulfamoyl group; a heterocyclic group such as a pyridyl group, a triazinyl group, and a benzothiazolyl group; a nitro group; and a halogen atom such as a fluorine atom, a chlorine atom, a bromine atom, and a iodine atom.

$R_3$ and $R_4$ may be an alkyl group having 1 to 12 carbon atoms, an aryl group, a heterocyclic group, an amino group, a hydroxyl group, a cyano group, or a carbamoyl group, such as an alkyl group having 1 to 4 carbon atoms, an aryl group, a heterocyclic group, a cyano group, or a carbamoyl group. From the standpoint of easiness of synthesis, it may be the case that $R_3$ is a substituent such that a substituent constant according to a Hammett rule has a positive value.

The Hammett rule as referred to herein is an empiric rule suggested by L. P. Hammett in 1935 in order to consider quantitatively the effect produced by a substituent on a reaction or equilibrium of a benzene derivative. At present, this rule is widely considered to be adequate. The substituent constants of Hammett rule are described in various reports. See, for example, Inamoto Naoki "Hammett Rule—Structure and Reactivity—", published by Maruzen; "Lectures on New Experimental Chemistry 14—Synthesis and Reaction of Organic Compounds V", p. 2605 (by Japan Chemical Society, published by Maruzen); Nakaya Tadao "Theoretic Organic Chemistry Interpretation", p. 217 (Tokyo Kagaku Dojin), Chem. Rev., 91, 165 (1991). In the present invention, each substituent is limited and explained by a Hammett substituent constant $\sigma_p$, but it does not mean that the substituents are limited only to the substituents which have the well-known values presented in the reports. Even if a substituent value is not known from the reference sources, in a case where it is measured based on the Hammett rule, the substituent is also included in the scope of the invention. Examples of electron-withdrawing groups for which the Hammett substituent constant has a positive value include a nitro group: $\sigma_p=0.78$, a cyano group: $\sigma_p=0.66$, a sulfonic acid group: $\sigma_p=0.35$, a carboxylic acid group: $\sigma_p=0.45$, a carbamoyl group: $\sigma_p=0.36$, a sulfamoyl group: $\sigma_p=0.60$, a trifluoromethyl group: $\sigma_p=0.54$, a halogen atom (for example, a fluorine atom: $\sigma_p=0.06$, a chlorine atom: $\sigma_p=0.23$, a bromine atom: $\sigma_p=0.23$, a iodine atom: $\sigma_p=0.18$), a carboxylic acid ester group (for example, a carboxylic acid methyl ester: $\sigma_p=0.45$, a carboxylic acid ethyl ester: $\sigma_p=0.45$, a carboxylic acid phenyl ester: $\sigma_p=0.44$), a pyridyl group (for example, 2-pyridyl group: $\sigma_p=0.17$, 3-pyridyl group: $\sigma_p=0.25$, 4-pyridyl group: $\sigma_p=0.44$), a pyrimidyl group (for example, 2-pyrimidyl group: $\sigma_p=0.53$, 4-pyrimidyl group: $\sigma_p=0.63$, 5-pyrimidyl group: $\sigma_p=0.39$). In particular, in a case of general formula (I) in the present description, it may be that $R_3$ is a pyridyl group, a cyano group, or a carbamoyl group.

Cy in the general formula (I) in the present description represents an aryl group, and the aryl group may have a substituent. The aryl group is not particularly limited, and specific examples thereof include an aromatic carbocyclic group such as a phenyl group and a naphthyl group and an aromatic heterocyclic group such as an imidazolyl group, a thiazolyl group, an oxazolyl group, a pyrrolyl group, an oxadiazolyl group, a thiadiazolyl group, a pyrazolyl group, a 1,2,3-triazolyl group, a 1,2,4-triazolyl group, a furyl group, a thienyl group, a pyridyl group, a pyrimidinyl group, a pyrazinyl group, a pyridazinyl group, a benzoimidazolyl group, and a benzothiazolyl group. From the standpoint of gas resistance and light fastness, it may be that Cy is an aromatic ring substituted with a carboxylic acid group or sulfonic acid group, or a nitrogen-containing aromatic heterocyclic group. It may also be the case that Cy is an aromatic ring substituted with a carboxylic acid group or sulfonic acid group, or a nitrogen-containing five-membered heterocyclic group.

Where the aforementioned general formula (I) includes at least one anionic group, water solubility can be improved. The anionic group is not particularly limited, and examples thereof include a carboxylic acid group, a sulfonic acid group, and a phosphoric acid group. Groups with a freed hydrogen and groups to which a counter ion has been added are also included. The counter ion is not particularly limited, and examples thereof include alkali metals such as lithium, sodium, and potassium; quaternary ammoniums such as ammonium methylammonium, dimethylammonium, trimethylammonium, tetramethylammonium, ethylammonium, diethylammonium, triethylammonium, tetraethylammonium, n-propylammonium, isopropylammonium, diisopropylammonium, n-butylammonium, tetra n-butylammonium, isobutylammonium, monoethanolammonium, diethanolammonium, and triethanolammonium. For example, counter ion may include a carboxylic acid group and a sulfonic acid group, such as a carboxylic acid group and a sulfonic acid group having counter ions such as an alkali metal ion such as sodium or potassium, or a quaternary ammonium ion.

A tautomer represented by the general formulas (VI) and (VII) below is present in the molecular structure represented by the general formula (I). The structure represented by the general formula (I) of the colorant compound in accordance with the invention also includes the structures represented by the general formulas (VI) and (VII) below.

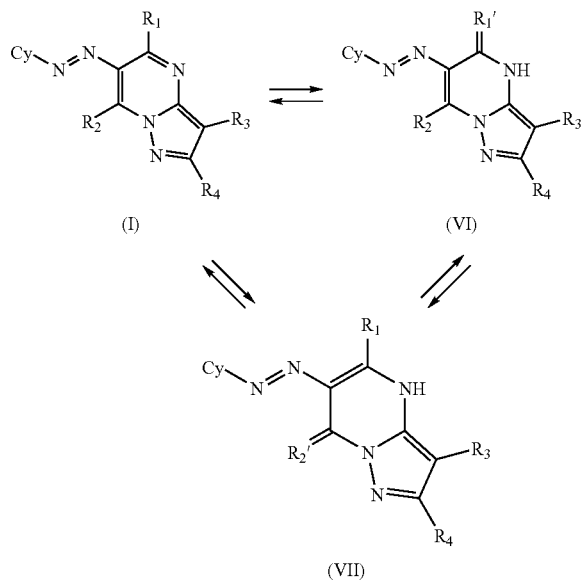

$R_1'$ and $R_2'$ in the colorant compound represented by the general formulas (VI) and (VII) denote either of an imino group and a carbonyl group that may be independently substituted. $R_1$ to $R_4$ and Cy have the same meaning as $R_1$ to $R_4$ and Cy in the general formula (I).

A method for manufacturing the colorant compound in accordance with aspects of the invention that has the structure represented by the general formula (I) will be described below.

The colorant compound in accordance with the invention that is represented by the general formula (I) can be synthesized by a well-known method. An example of the synthesis scheme is shown below.

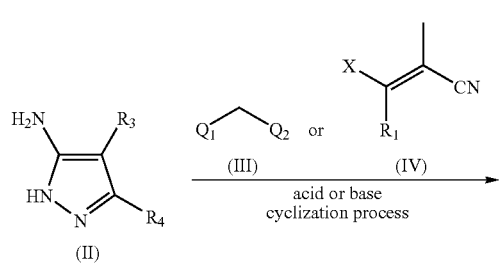

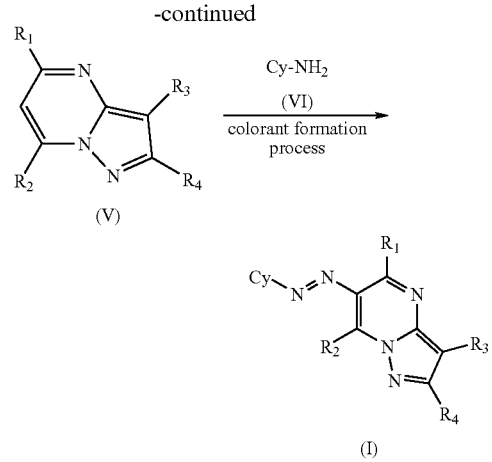

$R_1$ to $R_4$ and Cy in the general formulas (II) to (VI) above have the same meaning as $R_1$ to $R_4$ and Cy in the general formula (I). $Q_1$ and $Q_2$ independently represent any one from a cyano group, an alkylcarbonyl group, an arylcarbonyl group, and an alkoxycarbonyl group. X represents any elimination group.

The alkylcarbonyl group in $Q_1$ and $Q_2$ is not particularly limited, and examples thereof include an acetyl group, a propionyl group, a butyryl group, and a pentanoyl group.

The arylcarbonyl group in $Q_1$ and $Q_2$ is not particularly limited, and examples thereof include a benzoyl group and naphthylcarbonyl group.

Either of $Q_1$ and $Q_2$ is preferably a cyano group and an alkyl carbonyl group, more preferably an alkylcarbonyl group.

The elimination group in X is not particularly limited, and examples thereof include an amino group, an alkoxy group, a substituted amino group, and a halogen atom.

X is preferably an amino group, an alkoxy group, and a substituted amino group, more preferably an amino group and an alkoxy group having 1 to 4 carbon atoms.

First, a cyclization process of manufacturing a pyrazolopyrimidine derivative (V) by a reaction of an aminopyrazole derivative (II) and compounds represented by the general formula (III) or (IV) will be described.

Many types of the aminopyrazole derivative (II) used in accordance with the invention are marketed and can be easily purchased. This derivative can be also easily synthesized by a well-known method (for example, see J. Heterocycl. Chem., vol. 12, p. 1199-1205 (1975), JP-A No. 5-17470).

The specific examples of the aminopyrazole derivative (II) used in accordance with the invention are shown below, but these examples are not limiting.

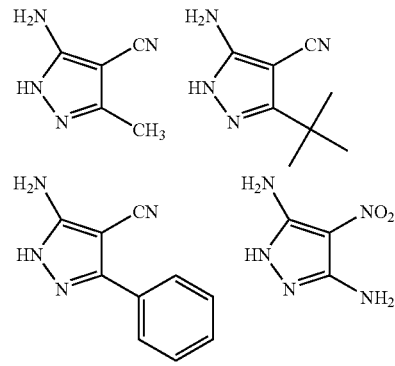

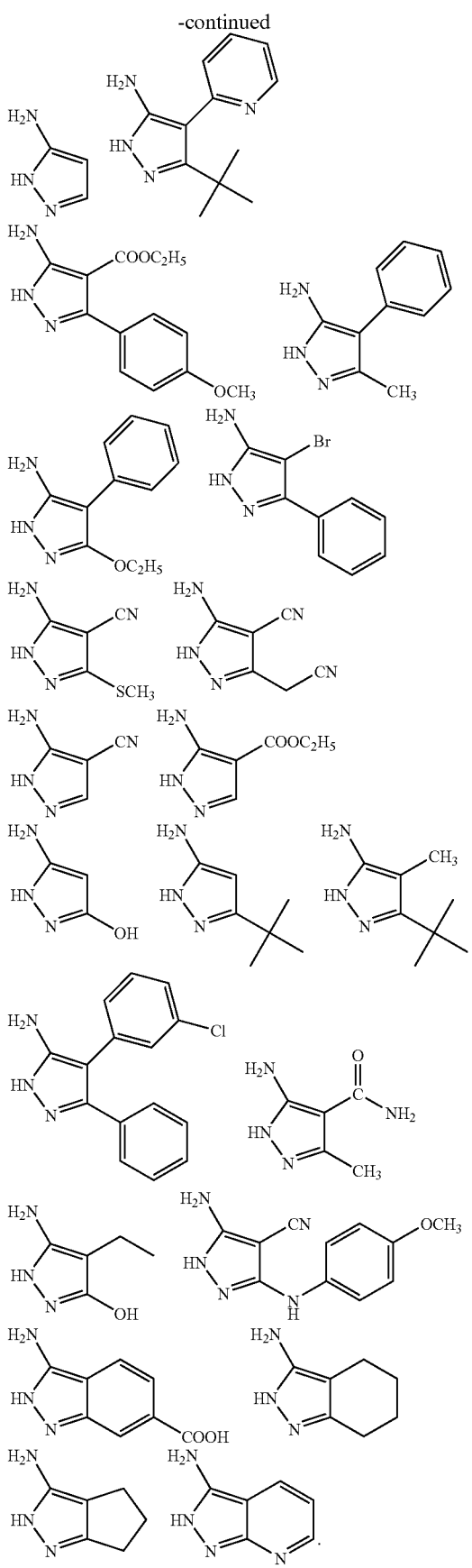

The present process can be conducted without a solvent, but a solvent may also be present. The solvent is not particularly limited, provided that that it does not participate in the reaction. Examples of suitable solvents include ester solvents such as methyl acetate, ethyl acetate, isopropyl acetate, and butyl acetate, a nitrile solvent such as acetonitrile, propionitrile, and benzonitrile, aromatic solvents such as benzene, toluene, xylene, ethylbenzene, and chlorobenzene, and mesitylene, ether solvents such as diisopropyl ether, methyl-tert-butyl ether, and tetrahydrofuran, alcohol solvents such as methanol, ethanol, n-propyl alcohol, iso-propyl alcohol, butyl alcohol, and diethylene glycol, and water. For example, the solvents may be alcohol solvents such as methanol, ethanol, n-propyl alcohol, iso-propyl alcohol, butyl alcohol, and diethylene glycol, and water, and even ethanol, iso-propyl alcohol, and diethylene glycol. Two or more solvents can be used in a mixture, and a mixing ratio of alcohols in a case they are used in a mixture can be set at random. The amount of the reaction solvent used is within a range of 0.1 to 1000 parts by weight, such as 0.5 to 500 parts by weight, and even 1.0 to 150 parts by weight per 1 part by weight of the aminopyrazole derivative (II).

The reaction temperature of the process is within a range of −80° C. to 250° C., preferably −50° C. to 200° C., such as −20° C. to 150° C. The reaction is usually completed within 24 hours.

A reaction rate in the process may be increased by adding an acid or a base. The acid used is not limited, provided that it does not participate in the reaction. Examples of suitable inorganic acids include hydrochloric acid, sulfuric acid, and phosphoric acid. Examples of suitable organic acids include p-toluenesulfonic acid, formic acid, acetic acid, propionic acid, and trifluoroacetic acid. Also strongly acidic ion-exchange resins such as Amberlite (Rohm and Haas Co.) and Amberlyst (Rohm and Haas Co.) and inorganic acid salts such as ammonium formate and ammonium acetate can be used. For example, the acids may be at least one of inorganic acid salts such as ammonium formate and ammonium acetate, such as ammonium acetate. The amount of the acid used is 0.1 to 50 mole, such as 1 to 30 mole, and even 2 to 10 mole per 1 mole of the aminopyrazole derivative (II).

Specific examples of the base that can be used in the present process include metal alkoxides such as potassium tert-butoxide, sodium tert-butoxide, sodium methoxide and sodium ethoxide; organic acid salts such as piperidine, pyridine, 2-methylpyridine, diethylamine, triethylamine, isopropylethylamine, potassium acetate and 1,8-diazabicyclo[5,4,0]undeca-7-ene (abbreviated hereinbelow as DBU); organic bases such as n-butyllithium and tert-magnesium chloride; and inorganic bases such as sodium borohydride, metallic sodium, sodium hydride, and sodium carbonate. For example, the bases may be at least one of potassium tert-butoxide, sodium methoxide, and sodium ethoxide, and piperidine, such as sodium methoxide and piperidine. The amount of the base used is 1 to 15 mole, such as 1.1 to 8 mole, and even 1.2 to 4 mole per 1 mole of the aminopyrazole derivative (II).

Upon completion of the reaction, the pyrazolopyrimidine derivative (V) can be obtained by dilution with water or precipitation with hydrochloric acid.

The colorant formation process will be described below. The colorant formation process can be implemented by a well-known method. Thus, the colorant compound (I) is obtained by coupling the pyrazolopyrimidine derivative (V) and a diazo compound derived from the amine derivative (VI). For example, the below-described method can be used as a specific coupling method. First, the amine derivative (VI)

is reacted with a nitrite such as sodium nitrite in the presence of an inorganic acid such as hydrochloric acid or sulfuric acid to convert the derivative into a corresponding diazonium salt. Then, the diazonium salt is coupled to the pyrazolopyrimidine derivative (V) to produce the colorant compound (I).

The obtained pyrazolopyrimidine derivative (V) and colorant compound (I) can be isolated and purified by the usual methods used for isolating and purifying organic compounds. For example, the reaction liquid is made acidic with hydrochloric acid or the like, solids are filtered off by acid precipitation, neutralization with sodium hydroxide or the like is conducted, and subsequent concentration produces a crude product. The crude product is then recrystallized using acetone or methanol and purified by column purification using silica gel. A high-purity product can be obtained by conducting purification by using the above-described methods individually or in combination.

The above-described manufacturing method makes it possible to synthesize the colorant compound represented by the general formula (I) below. Colorant compounds (I-1) to (I-25) are presented below as specific examples of the colorant compound in accordance with the invention, but these examples are not limiting. In the colorant compounds (I-1) to (I-23), $R_1$, $R_2$, $R_3$, $R_4$, and Cy in the general formula (I) below are substituents presented in Tables 1 to 3.

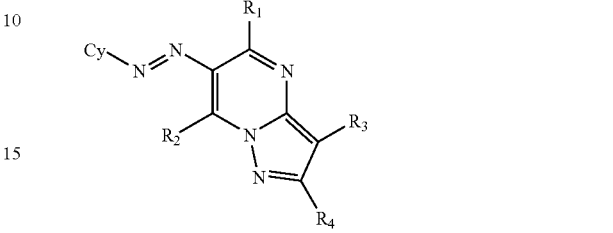

General Formula (I)

TABLE 1

| Compound Number | R1 | R2 | R3 | R4 | Cy |
|---|---|---|---|---|---|
| I-1 | —OH | —OH | —CN | —CH$_3$ | 2-methyl-5-sulfonato-benzoate (SO$_3$Na, ONa) |
| I-2 | —CH$_3$ | —NH$_2$ | —CN | —CH$_3$ | 2-methyl-5-sulfonato-benzoate (SO$_3$Na, ONa) |
| I-3 | —OH | —NH$_2$ | —CN | —CH$_3$ | 2-methyl-5-sulfonato-benzoate (SO$_3$Na, ONa) |
| I-4 | —CH$_3$ | —OH | —CN | —CH$_3$ | 2-methyl-5-sulfo-benzoic acid (SO$_3$H, OH) |
| I-5 | —OH | —OH | —C(=O)NH$_2$ | —CH$_3$ | 2-methyl-5-sulfonato-benzoate (SO$_3$Na, ONa) |

TABLE 1-continued

| Compound Number | R1 | R2 | R3 | R4 | Cy |
|---|---|---|---|---|---|
| I-6 | —OH | —OH | —CN | —C(CH₃)₃ | 2-methyl-5-sulfonato-benzoate (Na salts) |
| I-7 | phenyl | —CH₃ | —CN | —CH₃ | 2-methylbenzoate (Na salt) |
| I-8 | —OH | —OH | —CN | —CH₃ | 4-methylbenzoate (Na salt) |

TABLE 2

| Compound Number | R1 | R2 | R3 | R4 | Cy |
|---|---|---|---|---|---|
| I-9 | —OH | —NH₂ | —CN | —CH₃ | 3-methylbenzoate (Na salt) |
| I-10 | —OH | —OH | —CN | —CH₃ | 2-methyl-6-sulfonato-benzothiazole (Na salt) |
| I-11 | —OH | —OH | —C(O)OC₂H₅ | 4-methoxyphenyl | 2-methyl-5-sulfonato-benzoate (Na salts) |
| I-12 | —OH | —OH | —CN | —SCH₃ | 2-methyl-5-sulfonato-benzoate (Na salts) |
| I-13 | —OH | —OH | —CN | —CH₃ | 1-(3-sulfonatophenyl)-3,5-dimethylpyrazole (Na salt) |

TABLE 2-continued

| Compound Number | R1 | R2 | R3 | R4 | Cy |
|---|---|---|---|---|---|
| I-14 | —OH | —OH | —CN | —CH$_3$ | 2,5-dichloro-4-methylphenyl-SO$_3$Na |
| I-15 | —OH | —OH | —NO$_2$ | —NHC(O)CH$_3$ | 2-methyl-5-sulfonato(Na) benzoate(Na) |
| I-16 | —OH | —OH | 2-pyridyl | phenyl | 2-methyl-5-sulfonato(Na) benzoate(Na) |

TABLE 3

| Compound Number | R1 | R2 | R3 | R4 | Cy |
|---|---|---|---|---|---|
| I-17 | —CH$_3$ | —NH$_2$ | —H | —C(CH$_3$)$_3$ | 2-methyl-5-sulfonato(Na) benzoate(Na) |
| I-18 | —OH | —OH | —Cl | —OC$_2$H$_5$ | 2-methyl-5-sulfonato(Na) benzoate(Na) |
| I-19 | —OH | —OH | 4-chlorophenyl | phenyl | 2-methyl-5-sulfonato(Na) benzoate(Na) |
| I-20 | —OH | —OH | —H | —OH | 2-methyl-5-sulfonato(Na) benzoate(Na) |

TABLE 3-continued

| Compound Number | R1 | R2 | R3 | R4 | Cy |
|---|---|---|---|---|---|
| I-21 | —CH₃ | —NH₂ | —H | (tolyl) | (2-methyl-5-sulfonato-benzoate sodium) |
| I-22 | —OH | —OH | —H | —OH | (2-methyl-5-sulfonato-benzoate sodium) |
| I-23 | —OH | —OH | —CN | —CH₃ | (3-methylbenzoate sodium) |

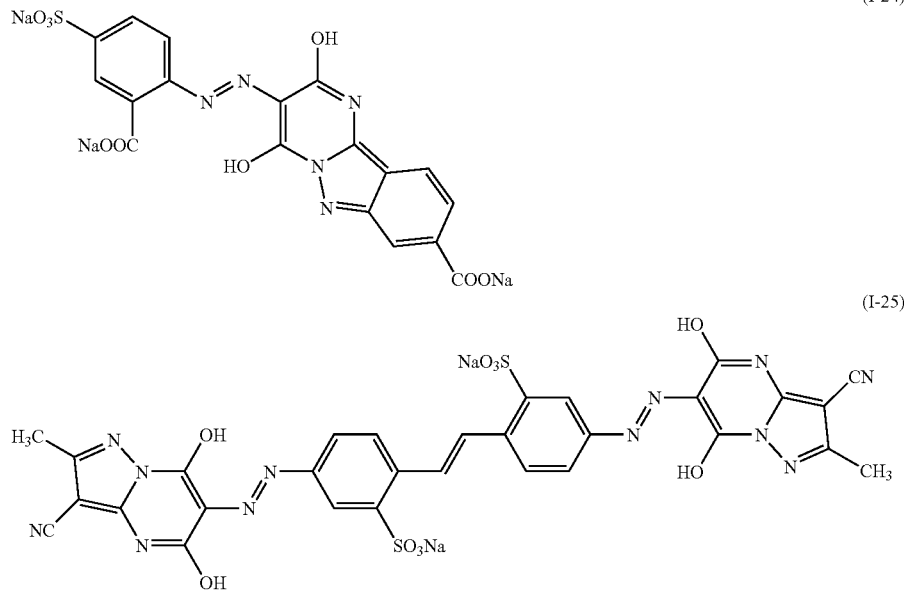

(I-24)

(I-25)

The colorant compound in accordance with the invention has a bright color tone, and spectral characteristics thereof enable the use as a coloring agent, preferably as a coloring agent for recording image information. This application is described below in greater detail.

Ink

The colorant compound in accordance with aspects of the invention may have a bright color tone and excellent spectral characteristic thereof enables the use as a coloring agent of yellow, magenta, or black color, preferably as a material for recording image information. More specifically, the colorant compound in accordance with the invention can be advantageously used as a material (color material) for ink for ink jet recording and also printing ink, and ink for coating material and writing utensils.

A method for manufacturing an ink that contains a colorant compound in accordance with aspects of the present invention that can be advantageously used as ink for ink jet recording will be explained below. An ink composition that can be used as ink can be produced by dissolving or dispersing the colorant compound represented by the general formula (I) in a liquid medium. For example, an aqueous medium be used as the liquid medium. When ink for ink jet recording is produced, it may be that the colorant compound is contained in an amount within a range of equal to or greater than 0.2 part by weight and equal to or less than 10 parts by weight in 100 parts by weight of the ink.

Water or a mixed medium of water and a water-soluble organic solvent can be used as the aforementioned aqueous medium. The water-soluble organic solvent that can be used in this case is not particularly limited, provided that it is soluble in water. Examples of suitable solvents include alcohol, polyhydric alcohols, polyglycols, glycol ethers, nitrogen-containing polar solvents, and sulfur-containing polar solvents. With consideration for preservation of moisture retaining ability of the ink, improvement of coloring material dissolution ability, and effective permeation of the ink into the recording paper, the water-soluble organic solvent may be contained in the ink at a ratio within a range of equal to or greater than 1 wt. % and equal to or less than 40 wt %, such as equal to or greater than 3 wt. % and equal to or less than 30 wt % based on the entire ink. It may also be that the content of water in the ink is within a range of equal to or greater than 30 wt. % and equal to or less than 95 wt % based on the entire ink. With such ratios, it is possible to improve dispersivity or solubility of the coloring material including the colorant compound in accordance with aspects of the invention in the ink. In particular, a viscosity that enables stable ink discharge can be obtained and clogging of nozzle tips can be prevented when the ink is used for ink jet recording.

A chemically synthesized surfactant such as an ionic surfactant, a non-ionic surfactant, or a polymer surfactant can be used as a constituent component of the ink including the colorant compound in accordance with aspects of the present invention. Surfactants derived from natural products and obtained by modification thereof with enzymes or the like can be also used. These surfactants may be used singly or in combination. With the object of maintaining good dispersion stability of the colorant compound in accordance with the present invention, it may be that the total content of the surfactant in the ink is equal to or more than 0.5 wt. % to equal to or less than 20 wt. % based on the entire ink.

The type of the surfactant is not particularly limited. Examples of suitable ionic surfactants include anionic surfactants such as aliphatic monocarboxylic acid salts, polyoxyethylene alkyl ether carboxylic acid salts; N-acyl sarcosine salts, N-acylglutamic acid salts, dialkylsulfosuccinic acid salts; alkanesulfonic acid salts, alpha-olefinsulfonic acid salts, straight-chain or branched alkylbenzenesulfonic acid salts, naphthalenesulfonic acid salt formaldehyde condensates, alkylnaphthalenesulfonic acid salts; N-methyl-N-acyltauric acid salts; alkylsulfuric acid salts, polyoxyethylene alkyl ether sulfuric acid salts, oil-and-fat sulfuric acid ester salts; and alkylphosphoric acid salts, polyoxyethylene alkyl ether phosphoric acid salts, and polyoxyethylene alkylphenyl ether phosphoric acid salts; cationic surfactants such as alkylamine salts, alkyltrimethylammonium chloride, alkyltrimethylammonium bromide, or alkyltrimethylammonium iodide, dialkyldimethylammonium chloride, dialkyldimethylammonium bromide, or dialkyldimethylammonium iodide, alkylbenzalconium chloride, and alkylpyridinium chloride; amphoteric surfactants such as alkylbetaines, fatty acid amidopropylbetaines, 2-alkyl-N-carboxymethyl-N-hydroxyethyl imidazolinium betaines, alkyl or dialkyldiethylenetriamine acetic acids, and alkylamineoxides.

Examples of nonionic surfactants include glycerin fatty acid esters, sorbitan fatty acid esters, sugar fatty acid esters; polyoxyethylene alkyl ethers, polyoxyethylene alkyl phenyl ethers, polyoxyethylene polyoxypropylene glycol; fatty acid polyethylene glycol, fatty acid polyoxyethylene sorbitan, and fatty acid alkanolamides.

Examples of polymeric surfactants include anionic polymers such as polyacrylic acid salts, styrene—acrylic acid copolymer salts, vinyl naphthalene—acrylic acid copolymer salts, styrene—maleic acid copolymer salts, vinyl naphthalene—maleic acid copolymer salts, and polyphosphoric acid; and nonionic polymers such as polyvinyl alcohol, polyvinyl pyrrolidone, and polyalkylene glycol.

Examples of surfactants derived from natural products and obtained by modification thereof with enzymes or the like include proteins such as gelatin and casein; natural gums such as Arabia gum; glucoside, e.g. saponin, cellulose derivatives such as alkylcellulose, carboxyalkylcellulose, and hydroxyalkylcellulose; ligninsulfonic acid salts; natural polymers such as shellac, and surfactants for food products, such as lecithin and fermented lecithin.

A pH value of ink when the ink is manufactured using the colorant compound in accordance with the present invention is not particularly limited, but from the standpoint of handleability a range of pH 4.0-11.0 may be provided. When ink for ink jet recording is produced, a moisture-retaining solid component such as urea, an urea derivative, and trimethylolpropane may be used as an ink component to maintain the moisture-retaining ability of the ink. The content of the moisture-retaining solid component such as urea, an urea derivative, and trimethylolpropane in the ink may be within a range of equal to or greater than 0.1 wt. % to equal to or less than 20 wt. %, such as equal to or greater than 3.0 wt. % and equal to or less than 10.0 wt. %.

When ink is produced various kinds of additives may be added, if necessary, to the above-described components, examples of the additives including a pH adjusting agent, a corrosion inhibitor, a preservative, an antimold agent, an antioxidant, a reduction preventing agent, an evaporation enhancer, a chelating agent, and a water-soluble polymer.

As described hereinabove, the ink prepared using the colorant compound in accordance with aspects of the invention can be especially advantageously used in an ink jet recording system in which recording is conducted by ejecting droplets by the action of thermal energy. The colorant compound in accordance with aspects of the invention can be also used as ink suitable for other ink jet recording methods and materials for general writing utensils or the like. Furthermore, the colorant material in accordance with aspects of the present invention is not limited to applications as a coloring agent and can find applications as an electronic material such as a colorant for optical recording or a colorant for a color filter.

EXAMPLES

The invention will be explained below in greater detail by examples thereof, but the invention is not limited to the examples. In the text below, "part" and "%" stand for parts by weight and wt. %, unless stated otherwise. The reaction products obtained are identified by a plurality of analytical methods using the below-described devices. Thus, the analytical devices used include: $^1$H and $^{13}$C nuclear magnetic resonance spectral analyzer (ECA-400, manufactured by JEOL Ltd.), high-speed liquid chromatograph (LC-20A, manufactured by Shimadzu Corp.), LC/TOF MS (LC/MSD TOF, Agilent Technologies Inc.), UV/Vis spectral photometer (U-3310 Spectral Photometer, manufactured by Hitachi, Ltd.).

Example 1

Synthesis Example 1

Synthesis of Colorant Compound (I-1)

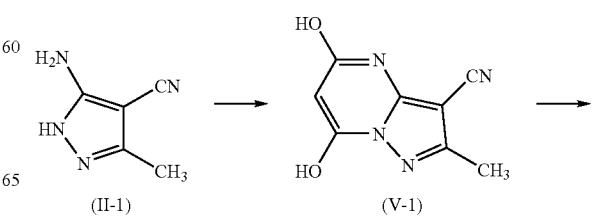

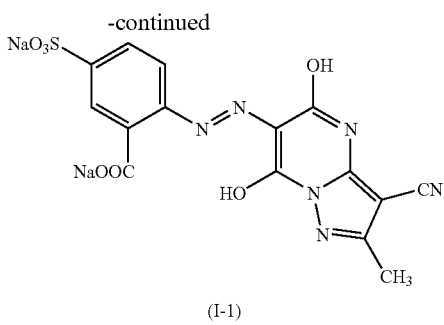

(I-1)

A solution total of 99.6 g (731 mmol) of 2-(1-ethoxyethylidene)malononitrile in 400 mL of ethanol was cooled to a temperature of 0 to 5° C., and 37 g (739 mmol) of hydrazine monohydrate was dropwise added to the solution. Upon completion of dropwise addition, the temperature of the reaction liquid was gradually raised to room temperature and then stirring was conducted for 7 hours under refluxing. Upon completion of the reaction, ethanol and excess hydrazine monohydrate were distilled off under reduced pressure, the residue was dispersed with water, and the solids obtained were filtered to obtain 60.6 g (yield 72.4%) of 5-amino-3-methyl-1H-pyrrazole-4-carbonitrile (II-1).

A total of 10 g (62 mmol) of diethyl malonate and 10 g (185 mmol) of sodium ethoxide were added to a solution of 7.2 g (59 mmol) of the obtained compound (II-1) in 140 mL of an ethanol solution, and refluxing was conducted for 5 hours. Upon cooling to room temperature, acid precipitation was conducted with hydrochloric acid and 6.6 g of 5,77-dihydroxy-2-methylpyrazolo[1,5-α]pyrimidine-3-carbonitrile (V-1) was obtained.

A total of 16 g of 35% hydrochloric acid was added to a solution of 12 g (54 mmol) of 5-sulfo anthranilic acid in 200 mL of water and the solution was cooled to a temperature equal to or lower than 5° C. A total of 3.9 g of sodium nitrite was gradually added to the solution, stirring was conducted for 1 hour, and then 0.75 g of amidosulfuric acid was added, the excess sodium nitrite was decomposed, and a diazo liquid A was obtained.

A total of 19.3 g (0.18 mmol) of sodium carbonate was gradually added to a solution of 5.0 g (26 mmol) of the obtained compound (V-1) in 80 mL of water, and the solution was cooled to a temperature equal to or lower than 5° C. The diazo liquid A was then gradually dropwise added so as to maintain the temperature at a level equal to or lower than 5° C., and the reaction was then conducted for 8 hours at a temperature of 0 to 5° C. Upon completion of the reaction, the pH was adjusted to a value equal to or less than 1 with hydrochloric acid, and the precipitated solids were filtered. The solids obtained were then dispersed in 200 mL of water, neutralized with an aqueous solution of sodium hydroxide and dissolved. The aqueous solution obtained was demineralized by electrodialysis and then crystallized from acetone to obtain 7.7 g (yield 65.5%) of a target compound (I-1). Analysis conducted with the above-described devices confirmed that the compound obtained had the above-described structure. The analysis results are presented below.

[Analysis Results for the Colorant Compound (I-1)]

[1] $^1$H NMR (400 MHz, DMSO-$d_6$, room temperature): δ [ppm]=2.22 (s, 3H), 7.67 (d, 1H), 7.83 (d, 1H), 8.31 (d, 1H); the results are shown in FIG. 1.

[2] Mass analysis (ESI-TOF): m/z=439.0089 (M-Na)$^-$, 417.0286 (M-2Na)$^{2-}$.

[3] HPLC results: purity=98.4 area %, holding time 10.9 min (0.1 mM, TFA solution-MeOH).

[4] UV/Vis spectral analysis: $\lambda_{max}$=412.0 nm.

Synthesis Example 2

Synthesis of Colorant Compound (I-2)

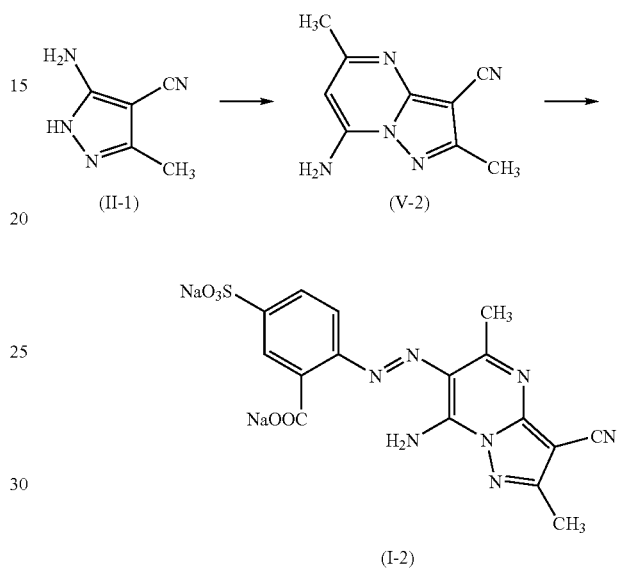

(I-2)

A solution of 7 g (purity 96.0%, 81.8 mmol) of 3-amino-2-butenenitrile, 10 g (purity 95.4%, 81.8 mmol) of compound (II-1), and 6 g of ammonium acetate in 50 mL of diethylene glycol were stirred for 22 hours under refluxing. Upon completion of the reaction, 12.4 g of 7-amino-2,5-dimethylpyrazolo[1,5-α]pyrimidine-carbonitrile (V-2) was obtained by dilution with 200 mL of water and filtration of solids.

A total of 16 g of 35% hydrochloric acid was added to a solution of 12 g (54 mmol) of 5-sulfo anthranilic acid in 200 mL of water and the solution was cooled to a temperature equal to or lower than 5° C. A total of 3.9 g of sodium nitrite was gradually added to the solution, stirring was conducted for 1 hour, and then 0.75 g of amidosulfuric acid was added, the excess sodium nitrite was decomposed, and a diazo liquid A was obtained.

A total of 17 g (0.16 mmol) of sodium carbonate was gradually added to a solution of 4.9 g (purity 95.4%, 25.5 mmol) of the obtained compound (V-2) in 60 mL of dimethylformamide (abbreviated hereinbelow as DMF). The diazo liquid A cooled to a temperature equal to or lower than 5° C. was then gradually dropwise added, and the reaction was then conducted for 8 hours at room temperature. Upon completion of the reaction, DMF and water were concentrated under reduced pressure, followed by dilution with hydrochloric acid and filtration of precipitated solids. The filtered solids were then dispersed in 200 mL of water, neutralized with an aqueous solution of sodium hydroxide, and dissolved. The aqueous solution obtained was demineralized by electrodialysis and then crystallized from acetone to obtain 1.6 g (yield 13.6%) of a target compound (I-2).

23

[Analysis Results for the Colorant Compound (I-2)]

[1] $^1$H NMR (400 MHz, DMSO-$d_6$, room temperature): δ [ppm]=2.27 (s, 3H), 2.30 (s, 3H), 7.43-7.50 (m, 3H), 7.61 (dd, 1H, J=7.33, 14.7 Hz), 7.79 (s, 1H).

[2] Mass analysis (ESI-TOF): m/z=436.0373 (M-Na)$^-$, 414.0550 (M-2Na)$^{2-}$.

[3] HPLC results: purity=96.1 area %, holding time 14.9 min (0.1 mM, TFA solution-MeOH).

[4] UV/Vis spectral analysis: $\lambda_{max}$=375 nm.

Synthesis Example 3

Synthesis of Colorant Compound (I-3)

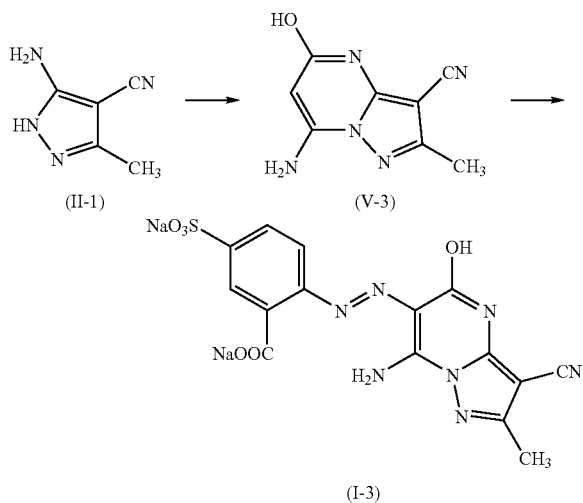

A total of 10 g (purity 98.1%, 82.5 mmol) of ethylcyanoacetate and 9.3 g (173 mmol) of sodium ethoxide were added to a solution of 10 g (purity 98.0%, 86.6 mmol) of compound (II-1) in 140 mL of ethanol, followed by refluxing for 5 hours. After cooling to room temperature, precipitation with hydrochloric acid produced 10.4 g of 7-amino-5-hydroxy-2-methylpyrazolo[1,5-α]pyrimidine-3-carbonitrile (V-3).

A solution of 12 g (54 mmol) of 5-sulfo anthranilic acid in 120 mL of DMF was cooled to a temperature equal to or lower than 5° C. A total of 20 mL of DMF solution of 40% nitrosylsulfuric acid was gradually dropwise added and stirring was conducted for 1 hour so as to maintain the temperature equal to or lower than 5° C. Then, 0.75 g of amidosulfuric acid was added, the excess nitrosylsulfuric acid was decomposed, and a diazo liquid B was obtained.

A solution of 5.0 g (26 mmol) of the obtained compound (V-3) in 80 mL of DMF was cooled to a temperature equal to or lower than 5° C. Then, the diazo liquid B was gradually dropwise added, so as to maintain the temperature equal to or lower than 5° C., and the reaction was then conducted for 8 hours at a temperature of 0-5° C. Upon completion of the reaction, the solvent was distilled off under reduced pressure, and then pH was adjusted to a value equal to or lower than 1 with hydrochloric acid and the precipitated solids were filtered. The filtered solids were then dispersed in 200 mL of water, neutralized with an aqueous solution of sodium hydroxide, and dissolved. The aqueous solution obtained was demineralized by electrodialysis and then crystallized from acetone to obtain 7.2 g (yield 61.3%) of a target compound (I-3).

24

[Analysis Results for the Colorant Compound (I-3)]

[1] $^1$H NMR (400 MHz, DMSO-$d_6$, room temperature): δ [ppm]=2.28 (s, 3H), 7.59-7.70 (m, 1H), 8.05-8.07 (m, 1H), 8.29-8.35 (m, 1H).

[2] Mass analysis (ESI-TOF): m/z=416.0440 (M-2Na)$^{2-}$.

[3] HPLC results: purity=98.2 area %, holding time 9.1 min (0.1 mM, TFA solution-MeOH).

[4] UV/Vis spectral analysis: $\lambda_{max}$=419 nm.

Other Synthesis Examples

Colorant compound (I-1) to (1-25) presented in Table 1 were obtained according to the methods described in Synthesis Examples 1-3.

Example 2

Ink Preparation Example 1

A total of 3.5 parts of the colorant compound (I-1) was added to 1 part of Acetylenol EH (manufactured by Kawaken Fine Chemical Co.), 7.5 part of ethylene glycol, 7.5 parts of glycerin, and 7.5 parts of urea, and ion-exchange water was then added to obtain a total of 100 parts. The components were then thoroughly stirred and dissolved to produce ink (A).

Ink Preparation Examples 2 to 11

Inks (B) to (L) were prepared in the same manner as described above, except that the colorant compound (I-1) used in Ink Preparation Example 1 was replaced with colorant compounds (I-2), (I-3), (I-6), (I-8), (I-9), (I-13), (I-14), (I-16), (I-17), (I-21), and (I-23), respectively.

Comparative Ink Preparation Examples 1 to 4

Comparative inks (M) to (P) were prepared in the same manner as described above, except that the colorant compound (I-1) used in Ink Preparation Example 1 was replaced with comparative colorant compounds (M-1) to (M-6), respectively. The comparative colorant compounds (M-5) and (M-6) did not contain a water-soluble substituent and, therefore, solubility in water was poor and inks could not be prepared.

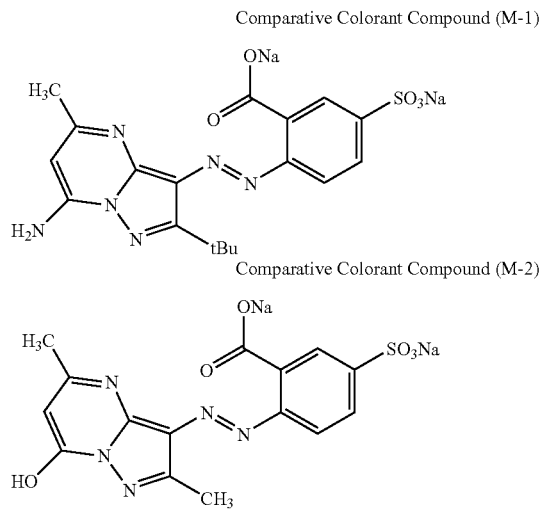

-continued

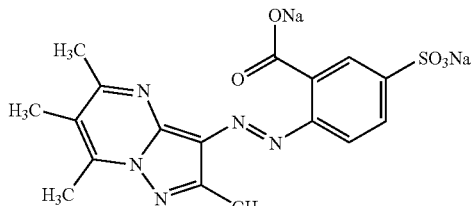

Comparative Colorant Compound (M-3)

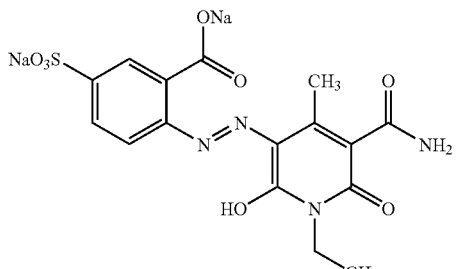

Comparative Colorant Compound (M-4)

Comparative Colorant Compound (M-5)

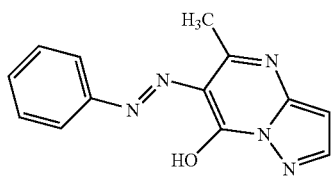

Comparative Colorant Compound (M-6)

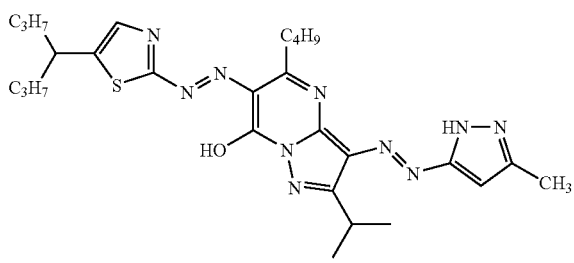

<Evaluation>

Inks (A) to (L) obtained in Ink Preparation Examples 1 to 11 and comparative inks (M) to (P) obtained in Comparative Ink Preparation Examples 1 to 4 were loaded in ink cartridges of an ink jet printer Pixus iP8600 manufactured by Canon Inc. Then, prints were produced by printing solid images in the form of squares with a side of 2 cm on glossy professional photopaper (PR-101) manufactured by Canon Inc. The prints were naturally dried for 24 hours to obtain prints for evaluation.

[Light Fastness]

The prints obtained were placed in an Atlas Weather-Ometer (Ci4000, manufactured by Toyo Seiki Seisakusho) and exposed for 50 h. The measurement conditions in this case were as follows: Black Panel: 50° C., Chamber: 40° C., Rel. Humidity: 70%, and Irradiance (340 nm): 0.39 W/m². The test paper was analyzed with SpectroLino (Gretag Macbeth Co) before and after the irradiation. Optical density and chromaticity (L*, a*, b*) in the L*a*b* color system were measured. A color difference (ΔE) was calculated by the following formula on the basis of measured value of color properties.

Color difference $(\Delta E) = \sqrt{\{(a^*(\text{before the test}) - a^*(\text{after the test}))^2 + (b^*(\text{before the test}) - b^*(\text{after the test}))^2 + (c^*(\text{before the test}) - c^*(\text{after the test}))^2\}}$ The evaluation was conducted in the following manner. Light fastness was determined to be good when ΔE was less than 10.

A: ΔE is less than 5.
B: ΔE is equal to or greater than 5 and less than 10.
C: ΔE is equal to or greater than 10.

[Gas Resistance]

The prints obtained were placed in an ozone weather-meter (OMS-H, manufactured by Suga Shikenki KK) and exposed for 4 hours under an atmosphere with an ozone concentration of 10 ppm, a temperature of 24° C., and a relative humidity of 60%. The reflection density of the prints was also measured before and after the test. The results obtained were estimated based on criteria similar to those of the light fastness test. A color difference (ΔE) was calculated by the following formula on the basis of measured value of color properties.

Color difference $(\Delta E) = \sqrt{\{(a^*(\text{before the test}) - a^*(\text{after the test}))^2 + (b^*(\text{before the test}) - b^*(\text{after the test}))^2 + (c^*(\text{before the test}) - c^*(\text{after the test}))^2\}}$ The evaluation was conducted in the following manner. Gas resistance was determined to be good when ΔE was less than 10.

A: ΔE is less than 5.
B: ΔE is equal to or greater than 5 and less than 10.
C: ΔE is equal to or greater than 10.

[Storage Stability]

Inks (A) to (L) obtained in, Ink Preparation Examples 1 to 11 and comparative inks (M) to (P) obtained in Comparative Ink Preparation Examples 1 to 4 were placed in sealed glass containers and allowed to stay for 1 month at a temperature of 60° C. Light absorbance (Abs) at a maximum absorption wavelength was then measured by UV/Vis spectral analysis and compared with a value (Abs0) obtained before the inks were allowed to stay for 1 month at a temperature of 60° C.

The evaluation was conducted in the following manner, and storage stability was determined to be good when Abs/Abs0 was equal to or greater than 0.90.

A: Abs/Abs0 is less than 0.95.
B: Abs/Abs0 is equal to or greater than 0.90 and less than 0.95.
C: Abs/Abs0 is equal to or less than 0.90.

Types of the colorants used in the inks and evaluation results relating to light fastness, gas resistance, and storage stability are shown in Table 4.

TABLE 4

| Ink | Compound number | Light fastness | Gas resistance | Storage Stability |
|---|---|---|---|---|
| (A) | Colorant compound (I-1) | A | A | A |
| (B) | Colorant compound (I-2) | B | A | A |
| (C) | Colorant compound (I-3) | B | A | A |
| (D) | Colorant compound (I-6) | A | A | A |
| (E) | Colorant compound (I-8) | A | A | A |
| (F) | Colorant compound (I-9) | B | A | A |
| (G) | Colorant compound (I-13) | A | A | A |
| (H) | Colorant compound (I-14) | A | A | A |
| (I) | Colorant compound (I-16) | A | A | A |
| (J) | Colorant compound (I-17) | B | A | A |
| (K) | Colorant compound (I-21) | B | B | A |
| (L) | Colorant compound (I-23) | A | A | A |
| (M) | Comparative colorant compound (M-1) | C | A | B |
| (N) | Comparative colorant compound (M-2) | C | C | A |

TABLE 4-continued

| Ink | Compound number | Light fastness | Gas resistance | Storage Stability |
|---|---|---|---|---|
| (O) | Comparative colorant compound (M-3) | C | C | A |
| (P) | Comparative colorant compound (M-4) | C | B | A |

Table 4 confirms that the inks using the colorant compounds in accordance with the present invention had good light fastness, gas resistance, and storage stability and, therefore, these colorant compounds are useful for inks.

The colorant compound in accordance is suitable for various applications. Thus, the colorant compound is not limited to applications as a coloring agent and can find applications as an electronic material such as a colorant for optical recording or a colorant for a color filter.

This application claims the benefit of Japanese Patent Application No. 2008-265177, filed Oct. 14, 2008, which is hereby incorporated by reference herein in its entirety.

What is claimed is:

1. A colorant compound represented by the general formula (I) below:

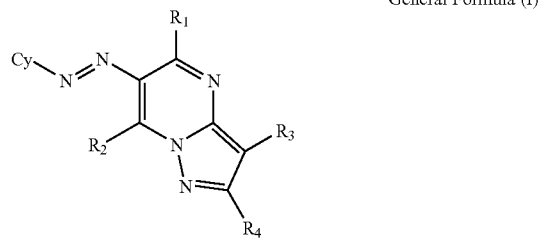

General Formula (I)

wherein in the general formula (I)

$R_1$ and $R_2$ represent independently from each other a species selected from at least one of an alkyl group, an aryl group, an aralkyl group, an alkoxy group, an aryloxy group, an amino group, and a hydroxyl group;

$R_3$ and $R_4$ represent independently from each other a species selected from at least one of a hydrogen atom, an alkyl group, an aryl group, a heterocycle group, an amino group, a hydroxyl group, a cyano group, an alkoxy group, an alkylsulfanyl group, a carboxylic acid group, a carboxylic acid ester group, a carboxylic acid thioester group, a carbamoyl group, a nitro group, and a halogen atom;

optionally, $R_3$ and $R_4$ may be bonded together to form an aromatic ring; and Cy represents an aryl group having at least one anionic group.

2. The colorant compound according to claim 1, wherein $R_3$ in the general formula (I) is a substituent for which a Hammett substituent constant has a positive value.

3. The colorant compound according to claim 1, wherein $R_3$ in the general formula (I) is a cyano group or a heterocyclic group.

4. The colorant compound according to claim 1, wherein either of $R_1$ and $R_2$ in the general formula (I) is a hydroxyl group.

5. The colorant compound according to claim 1, wherein $R_1$ and $R_2$ in the general formula (I) are each a hydroxyl group.

6. The colorant compound according to claim 1, wherein the general formula (I) includes a carboxylic acid group or a sulfonic acid group.

7. The colorant compound according to claim 1, wherein Cy in the general formula (I) is an aromatic ring substituted with a carboxylic acid group or a sulfonic acid group.

8. The colorant compound according to claim 1, wherein Cy in the general formula (I) is a nitrogen-containing aromatic heterocyclic group.

9. The colorant compound according to claim 1, wherein Cy in the general formula (I) is a nitrogen-containing aromatic five-membered hetero ring.

10. Ink comprising an aqueous medium and a colorant compound, wherein the colorant compound is the colorant compound according to claim 1.

11. The ink according to claim 10 for ink jet recording.

* * * * *